US008268630B2

(12) United States Patent
Fedder et al.

(10) Patent No.: US 8,268,630 B2
(45) Date of Patent: Sep. 18, 2012

(54) DIFFERENTIAL PRECONCENTRATOR-BASED CHEMICAL SENSOR STABILIZATION

(75) Inventors: Gary Keith Fedder, Turtle Creek, PA (US); Nathan Scott Lazarus, Pittsburgh, PA (US)

(73) Assignee: Carnegie Mellon University, Pittsburgh, PA (US)

( * ) Notice: Subject to any disclaimer, the term of this patent is extended or adjusted under 35 U.S.C. 154(b) by 324 days.

(21) Appl. No.: 12/831,590

(22) Filed: Jul. 7, 2010

(65) Prior Publication Data

US 2011/0010107 A1     Jan. 13, 2011

Related U.S. Application Data

(60) Provisional application No. 61/270,439, filed on Jul. 8, 2009.

(51) Int. Cl.
G01N 27/04 (2006.01)
G01N 27/22 (2006.01)

(52) U.S. Cl. ........ 436/149; 436/151; 436/174; 436/178; 436/181; 422/83; 422/88; 422/90; 702/22; 702/23; 702/24

(58) Field of Classification Search ............... 436/52, 436/149, 150, 151, 178, 181, 174; 422/50, 422/68.1, 82.01, 82.02, 83, 88, 90, 93, 98; 702/22, 23, 24, 25; 324/71.1
See application file for complete search history.

(56) References Cited

U.S. PATENT DOCUMENTS

| 4,410,632 | A | * | 10/1983 | Dilley et al. .......... 436/20 |
|---|---|---|---|---|
| 5,224,972 | A | | 7/1993 | Frye et al. |
| 5,589,396 | A | | 12/1996 | Frye et al. |
| 5,770,275 | A | | 6/1998 | Raman et al. |
| 6,171,378 | B1 | | 1/2001 | Manginell et al. |
| 6,171,865 | B1 | | 1/2001 | Weigl et al. |
| 6,850,859 | B1 | | 2/2005 | Schuh |
| 7,061,061 | B2 | | 6/2006 | Goodman et al. |
| 7,118,712 | B1 | | 10/2006 | Manginell et al. |
| 7,338,802 | B2 | | 3/2008 | Frischauf et al. |

OTHER PUBLICATIONS

Chang, Josephine Bea. "Functionalized polythiophene thin-film transistors for low-cost gas sensor arrays." Dissertation. UC Berkeley 2006.*
Davis, C. E. et al. "Enhanced detection of m-xylene using a preconcentrator with a chemiresistor sensor." Sensors and Actuators B (2005) 104 207-216.*
Alfeeli et al., "Multi-Inlet/Outlet Preconcentrator with 3-D μ-Structures Coated by Inkjet Printing of Tenax Ta", Solid-State Sensors, Actuators, and Microsystems Workshop, Jun. 1-5, 2008, pp. 118-121.
Creemer et al., "Titanium Nitride for MEMS Hotplates", Proceedings of the Semiconductor Advances for Future Electronics (SAFE), 2004, pp. 742-746.

(Continued)

Primary Examiner — Yelena G Gakh
Assistant Examiner — Christopher A Hixson
(74) Attorney, Agent, or Firm — The Webb Law Firm

(57) ABSTRACT

Sensor devices and sensing methods are provided. A sensor device is provided two flow channels, each comprising a sensor, and analyte flow is alternated between the two channels such that the sensors alternately serve as a sensor and a reference, thereby increasing accuracy of the sensors. The device is useful, for example, in chemical sensing using a variety of sensor types including without limitation: chemiresistors, gravimetric sensors, optical sensors, among others. Related sensing methods also are provided.

36 Claims, 14 Drawing Sheets

OTHER PUBLICATIONS

Fedder, "MEMS Fabrication", Proceedings of the IEEE International Test Conference, Sep. 30-Oct. 2, 2003, pp. 691-698.

Fedder, "CMOS-Based Sensors", Proceedings of the IEEE Sensors Conference, Oct. 31-Nov. 5, 2005, pp. 125-128.

Frye et al., "Controlled Microstructure Oxide Coatings for Chemical Sensors", Proceedings of the IEEE Solid State Sensors and Actuators Workshop, 1990, pp. 61-64.

Hierlemann et al., "Application-specific sensor systems based on CMOS chemical microsensors", Sensors and Actuators B, 2000, pp. 2-11, No. 70.

Hierlemann et al., "Higher-Order Chemical Sensing", Chem. Rev., 2008, pp. 563-613, vol. 108, No. 2.

Hierlemann, "CMOS-based Chemical Sensors", Advanced Micro and Nanosystems, 2005, pp. 335-390, vol. 2.

Lu et al., "Microporous Silica Prepared by Organic Templating: Relationship between the Molecular Template and Pore Structure", Chem. Mater, 1999, pp. 1223-1229, vol. 11, No. 5.

Manginell et al., "Microfabricated Planar Preconcentrator", Tech Digest Solid-State Sensor and Actuator Workshop, 2000, pp. 179-182.

Nieuwenhuizen et al., "Surface Acoustic Wave Chemical Sensors", Sensors and Materials, 1989, pp. 261-300, vol. 5.

Raman et al., "Template-Based Approaches to the Preparation of Amorphous, Nanoporous Silicas", Chem. Mater., 1996, pp. 1682-1701, vol. 8, No. 8.

Rodriguez et al., "Sampling Methods for Ion Mobility Spectrometers: Sampling, Preconcentration & Ionization", "http://www.foi.se/upload/LOTUS/D300.2_Sampling%20methods%20for%20Ion-%20Mobility%20Spectrometeres_PU.pdf", Jun. 30, 2009, 43 pages.

Rowe et al., "Single-Phase Synthesis of Functionalized Gold Nanoparticles", Chem. Mater., 2004, pp. 3513-3517, vol. 16., No. 18.

Spannhake et al., "High-temperature MEMS Heater Platforms: Long-term Performance of Metal and Semiconductor Heater Materials", Sensors, 2006, pp. 405-419, vol. 6.

Veeneman, "Design and Characterization of a Multi-Vapor Preconcentrator for a Micro-Scale Gas Chromatograph", University of Michigan Dissertation, 2009, 197 pages.

Weiss et al., "Inkjet Deposition System with Computer Vision-Based Calibration for Targeting Accuracy", Carnegie Mellon University Robotics Institute Tech. Report, Mar. 2006, 13 pages.

* cited by examiner

Chemical Concentration

R1

R2

R2-R1

DIFFERENTIAL PRECONCENTRATOR-BASED CHEMICAL SENSOR STABILIZATION

CROSS-REFERENCE TO RELATED APPLICATIONS

This application claims the benefit under 35 U.S.C. §119(e) to U.S. Provisional Patent Application No. 61/270,439, filed Jul. 8, 2009, which is incorporated herein by reference in its entirety.

STATEMENT REGARDING FEDERALLY-SPONSORED RESEARCH AND DEVELOPMENT

This invention was made with partial government support under NIOSH/CDC contract 200-2002-00528 and AFOSR Grant Number FA9550-07-1-0245. The government has certain rights in this invention.

This invention relates generally to the field of chemical sensing. In particular, it relates to methods of compensating for offset drift in chemical sensors and related apparatus.

Most chemical sensors experience drift, where the output of the sensor changes slowly with time, even with no chemical analyte present. This behavior can be due to many issues including temperature effects, packaging stress, material aging, oxidation of the material when exposed to air, and cumulative analyte permanently changing the sensing material. Uncompensated drift reduces the sensor resolution. Over time, the drift in many sensors can become very large.

Common-mode signals that cause drift, such as temperature and aging can be compensated, in principle, by differencing against a reference device. An impediment to using such a scheme is that the sensing and reference devices experience different environments since the reference is normally protected from the analyte, leading to mismatch of the devices' characteristics over time.

Individual chemical sensors tend to change their output due to environmental factors other than chemical analyte; as a result, there is no way to differentiate between a sudden pulse of gas molecules of interest and a sudden drift in offset due to other factors such as temperature and humidity. FIG. 1 shows a simple example illustrating this using a resistive chemical sensor. The sudden pulse in temperature and the sudden increase in chemical concentration are indistinguishable except for a scale factor.

Some types of chemical sensors use a differential measurement scheme to minimize offset drift. In this scheme, chemical sensor output is compared to a second, unexposed chemical sensor. Effects common to both chemical sensors, such as temperature, ideally will be completely removed, allowing a more accurate measurement. FIGS. 2A and 2B show two specific embodiments of this approach, one with two resistive sensors, one capped and one uncapped, measured separately, and the second with two resistive sensors in a voltage divider circuit and a simple example showing the effects of a temperature change. FIG. 2C shows a response to a sudden temperature change; since both sensors change with temperature, the output R2-R1 is unchanged.

However, ageing due to chemical exposure does not affect both chemical sensors; only the active sensor is exposed to chemicals. Creating a reference chemical sensor also requires a means of isolating the chemical sensor from the gas flow, often by a passivation layer or a cap. This means that the reference sensor will often experience some significant time delay before effects such as temperature begin to cancel out. Both chemical sensors will change their resistance similarly due to temperature; however, since the reference is under a cap, the reference sensor will take longer to change due to different thermal time constants for the two devices. FIG. 3 shows a timing diagram of a response to a temperature change that includes this effect.

Another problem that can occur with a non-hermetic capped reference sensor is that, over time, gas analyte such as humidity will leak into the cap. The time necessary to return to the initial output value can be as long as several hours. FIG. 4 shows the sensor output in this situation.

Another common scheme for both stabilization and sensitivity enhancement of chemical sensors compares the sensor output with a reference measurement taken with no analyte present. One method of obtaining this reference measurement is by using a preconcentrator, which are components that absorb chemical analyte in a preconcentrator material, such as activated carbon. The chemical analyte can be collected in the preconcentrator over a period of time, then the analyte can be released by heating in a concentrated pulse over a relatively short period. The heating pulse creates a corresponding pulse of concentrated analyte, which is the basis for the sensitivity enhancement. The sensor can be stabilized by differencing the sensor output before and during the pulse, creating a signal for the chemical concentration that is relative to any drift in the offset. However, with this time multiplexed scheme, the sensor baseline offset can become very large compared to the pulse signal, thus causing problems with implementing signal amplification. That is, small sense signals are often extracted from the difference of two large offset values. There will also be a time delay $\Delta t$ between the two samples, therefore there will also be a small error since the instantaneous drift will not be canceled out completely. The time delay may be on the order of seconds or even longer in order to average the signal to reduce noise. FIG. 5A shows a diagram of a pulse-stabilized system; FIG. 5B shows a sample timing diagram of this system, where the sensor resistance is shown decreasing upon analyte exposure. A. Hierlemann et al. (Chem. Rev. 2008, 108, 563-613) is a review paper that also covers a number of alternative techniques for compensating for baseline drift.

SUMMARY

The present invention describes systems, apparatuses, devices (systems, apparatuses and devices are considered to be synonymous and equally interchangeable) and methods for sensing which mitigate the effects of sensor drift over time. The devices and methods utilize two or more identical sensing devices where the roles each device plays, sensor or reference, are swapped periodically over time. Because all sensors are exposed the same when averaged over time, all will age and drift similarly.

According to one embodiment, this scheme is implemented in one non-limiting embodiment with two or more flow microchannels, each containing a sensing device and a preconcentrator. The analyte is released from the preconcentrator in only one of the two flow channels in a given measurement cycle. The sensor in this channel then detects the analyte, while the sensor device in the other channel acts as a reference. In one embodiment using two chemiresistors, the output from the two sensors is differenced through a voltage divider configuration. Two, three or more individual sensors may be employed in this scheme, each of which is exposed to the analyte essentially equally by rotating, shifting or otherwise changing the reference or testing sensor over time.

This setup compensates for sensor offset from temperature and aging over the lifetime of the device. The use of preconcentrators enables amplification of the ambient analyte concentration for enhanced sensitivity. This invention will result in an extended sensor system lifetime, a larger signal to noise and superior signal resolution.

DETAILED DESCRIPTION

The use of numerical values in the various ranges specified in this application, unless expressly indicated otherwise, are stated as approximations as though the minimum and maximum values within the stated ranges are both preceded by the word "about". In this manner, slight variations above and below the stated ranges can be used to achieve substantially the same results as values within the ranges. Also, unless indicated otherwise, the disclosure of these ranges is intended as a continuous range including every value between the minimum and maximum values.

Figure 6:
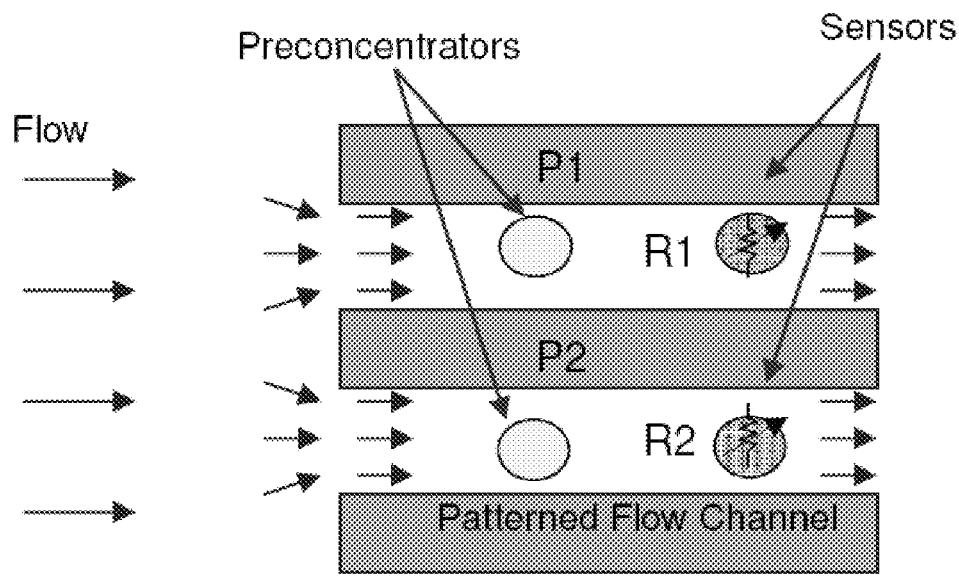
FIG. 6 illustrates the concept of the present invention of using two separate flow channels, each containing a preconcentrator and a chemical sensor.
Figure 7:
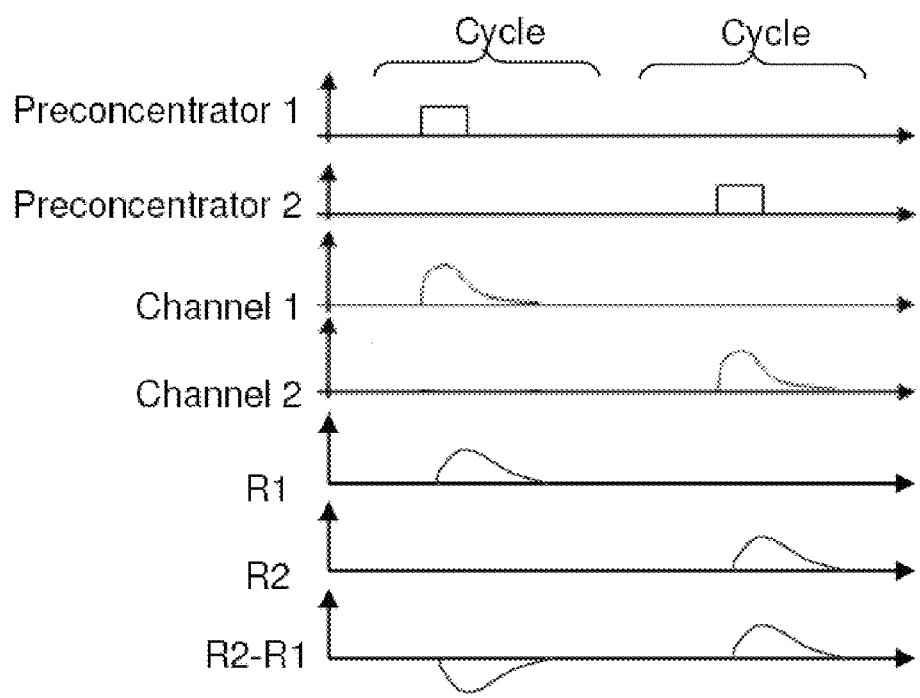
FIG. 7 provides a timing diagram from the use of the present invention.

Systems, apparatuses, and methods for chemical sensors which mitigate the effects of sensor drift over time are provided. The systems, apparatuses, and methods use two or more identical sensing devices where the roles each device plays, sensor or reference, are swapped periodically over time. Preconcentrators may be used to selectively expose the two chemical sensors as shown in FIG. 6. A simple timing diagram of the chemical sensor behavior is shown below, in FIG. 7.

Therefore according to one embodiment of a sensor device, the device comprises a first flow channel and a second flow channel which may be configured into a microdevice as described herein. The first flow channel comprises a first sensor and the second flow channel comprises a second sensor that is the same as the first sensor, meaning that the second sensor is essentially identical to the first sensor. In one embodiment, the sensors are made from the same lot of materials. The device comprises a controller, which may comprise any type of timing circuit or software, for periodically switching flow of analyte through the first and second flow channels so that the first and second sensors alternately serve as a sensor and a reference.

The device also comprises an analog or digital processor to conduct differencing of signals from the first sensor and the second sensor. The differencing may be conducted on raw signal output of the sensors or on amplified, stored (e.g. in memory), averaged, digitized, manipulated or otherwise modified output or output data from the sensors by any useful means. "Differencing" is an art-recognized term referring to obtaining a value or set of values indicative of the difference between two values, such as differences in the signal between two sources. Methods of differencing can vary greatly, including without limitation: analog methods derived, e.g., from electrical/electronic circuit/chip design, such as the resistive divider circuits described above and/or digital methods, derived from hardware and/or software implementations, as are broadly known. A processor for differencing signals can be any electrical, electronic or digital circuit, chip, hardware, software, etc. useful in differencing analog or digital signals or data obtained from sensors, such as, without limitation: direct sensor output, modified or amplified sensor output, output from more than one sensors that is unmodified or modified, stored sensor output data from one or more sensors over one or more data points, modified, analyzed or manipulated (e.g. averaged) stored sensor output data from one or more sensors over one or more data points etc.

In one implementation of the embodiment described above, the first flow channel comprises a first preconcentrator and the second flow channel comprises a second preconcentrator and the controller periodically switches flow of analyte through the first and second flow channel by releasing analyte periodically from the first preconcentrator and the second preconcentrator. The preconcentrator may comprise an adsorbent material and a heating element for desorbing analyte from the adsorbent material. The adsorbent material may comprise one or more of a porous polymer, graphitized carbon, a carbon molecular sieve, and a thick-film polymer. The heating element may be any useful design, such as a platinum heating element. The processor can conduct the differencing, for example, by a resistive divider, a capacitive divider or by measurement of resonant frequency. The sensors may be chemiresistor sensors, such as gold nanoparticle chemiresistors. The device may also comprise one or more heating elements adjacent to the sensors, and the controller periodically activates the one or more heating elements adjacent to the sensors to desorb analyte from the sensors. The device also may comprise flow sensors either in the flow channels or in any suitable place (in or about the flow channels), to determine when gas is flowing through channels of the device. In such a case, output of the flow sensors is used to control/trigger turning on of heaters to desorb analyte from the preconcentrator(s) and/or sensor(s) at (e.g.) a given flow rate. The device may be used to sense chemical(s) within a mask, such as a breathing mask, a gas mask or a respirator.

The device typically comprises a computer controller ("computer" is synonymous with "computing device" and can be virtually any form of computing device capable of outputting control signals, obtaining data or other information, analyzing, storing and/or manipulating data and/or functions of the devices, and which comprise a processor (e.g., microprocessor) and memory and input-output functionality). As would be evident to those of ordinary skill in the art, a controller as used herein can either directly or indirectly cause, control, activate etc. a function/activity, such as the heating of a heating element or the switching of a valve. For example, a controller causes a heating element to heat by either directly activating the heating element by (e.g.) directing current through a resistive heating element, or indirectly by triggering current to pass through a resistive heating element.

A data input and/or output interface (also referred to as a communications interface) typically is provided which is connected to the computer for transmitting data to and/or from the device. The interface may be a wireless interface, such as an IEEE 802.11 (e.g., 802.11(a), 802.11(b), 802.11(g) or 802.11(n) interface) or Bluetooth interface. The interface may be wired, such as a USB (e.g., USB 2.0), Ethernet, serial (e.g. RS232), GPIB (General Purpose Interface Bus, e.g. IEEE-488), or firewire interface.

A method for chemical sensing also is provided which employs a sensor device as described above comprising a first flow channel and a second flow channel, the first flow channel comprising a first sensor and the second flow channel comprising a second sensor that is the same as the first sensor. The method comprises controlling flow of an analyte through the first flow channel and the second flow channel in a manner such that the first and second sensors alternately function as a sensor and a reference; and differencing signals from the first sensor and the second sensor. Non-limiting examples of various embodiments of the sensor device are described above.

The systems, apparatuses and devices described herein are preferably fabricated as microfabricated devices (referred to herein as "microdevices" or "microsystems", referring generally to the small size of such systems, devices or apparatuses, and not inferring micrometer-scale or nanometer-scale dimensions). MEMS (microelectromechanical systems) or NEMS (nanoelectromechanical systems), comprising micron- or nanometer-scale mechanical parts/structures) devices are microdevices. Microfabrication methods and compositions useful for preparing the systems, apparatuses and devices described herein are well-known in the MEMS, NEMS, printed-circuit board (PCB) and integrated circuit (IC) manufacturing industries. Microsystems may be manufactured from a variety of materials. Common materials include silicon (e.g. polycrystalline silicon and silicon nitride), glass, carbon (e.g. carbon nanotube and graphene), diamond, polymers and metals. A variety of methods may be used to manufacture the apparatuses (See, e.g., G. Fedder, MEMS Fabrication, in Proceedings of the IEEE International Test Conference (ITC '03), Sep. 30-Oct. 2, 2003, Charlotte, N.C.; H. Baltes, et al., CMOS-MEMS, Wiley-VCH, ISBN 3257310800, January 2005). One such method is described in Example 1. Thin films are deposited by any of a variety of methods, for example and without limitation: physical vapor deposition (PVD), such as sputtering and evaporation; and chemical deposition, such as chemical vapor deposition (CVD), including low pressure CVD and plasma enhanced CVD, and thermal oxidation. Exemplary methods for patterning such devices include: mask lithography (photolithography), electron beam lithography, ion beam lithography, X-ray lithography, diamond patterning, injection molding, microstereolithography, silicon surface micromachining, high aspect ratio silicon micromachining and silicon bulk micromachining may be utilized. Structures may be formed by etching, including wet and dry etching methods. Wet methods include, without limitation: isotropic etching, anisotropic etching, HF etching and electrochemical etching. Dry etching methods include, without limitation: vapor etching, including xenon difluoride etching, plasma etching, including reactive ion etching and deep reactive ion etching (e.g., etching of silicon-on-insulator (SOI) and epitaxial silicon and single crystal reactive etch and metallization (SCREAM) methods). CMOS (complementary metal-oxide-semiconductor) structures/processes may be utilized (see, e.g., G. Fedder, CMOS Based Sensors, in Proceedings of the IEEE Sensors Conference (IEEE Sensors '05), pp. 125-128, Oct. 31-Nov. 3, 2005, Irvine, Calif. and G. K. Fedder, Sensors & Actuators A, vol. 57, no. 2, pp. 103-110, November 1996). Inkjet printing, for example inkjet printing methods using polymer dissolved in solvent, also can be used to deposit and pattern films (see, e.g., Alfeeli B., et al. Solid State Sensors, Actuators and Microsystems Workshop Hilton Head Island, South Carolina, Jun. 1-5, 2008, pages 118-121, for inkjet deposition of Tenax TA). Given the significant number of materials, methods and structural/topological variations possible, a person of skill in the field of microfabrication of microdevices (e.g., MEMS, NEMS and IC devices) may use any of a variety of methods and materials to produce/manufacture the microdevices described herein. U.S. Pat. Nos. 6,171,865, 6,850,859, 7,061,061 and 7,338,802, each of which is incorporated herein by reference for its technical disclosure, describe MEMS sensor systems, methods of manufacturing such systems, implementation and use of such systems.

The microdevices described herein include a number of substructures that can be formed by standard fabrication methods. Gas passes through two or more channels (passages, tubes, etc.) to contact the described sensors. Channels for the passage of a gas or liquid can be fluidly connected to other channels or substructures, which means that the gas or liquid can pass to or from the channel to or from another channel or substructure, such as a tube, inlet, outlet, etc., typically with minimal to no loss of the gas or liquid. Although unnecessary for certain embodiments of the systems, devices or apparatuses described herein, valves may be included. Any valve structure may be utilized, such as any of the number of valve mechanisms suitable for microdevices as are known in the art (see, e.g., U.S. Pat. No. 7,210,502).

In order to improve sample measurement and facilitate switching of sensors without use of valves, a preconcentrator is used in certain embodiments, which concentrates certain analytes, such as VOCs, and releases them in a controllable fashion. Virtually any device/structure that can absorb/adsorb a desired analyte and release that analyte in a controllable fashion would be useful. Useful preconcentrator sub-structures are well-known in the sensor and gas chromatography field (See, generally, Rodriguez, J. et al. D300.2: Sampling Methods For Ion Mobility Spectrometers: Sampling, Preconcentration & Ionization (30 Jun. 2009) Localisation of Threat Substances in Urban Society (LOTUS) FOI, Swedish Defence Research Agency, Tunba, Sweden (also describing sampling and ionization methods, http://www.foi.se/upload/LOTUS/D300.2_Sampling%20Methods%20for%20Ion%20Mobility%20Spectrometeres_PU.pdf), and Veeneman, R. A., Design and Characterization of a Multi-Vapor Preconcentrator for a Micro-Scale Gas Chromatograph (2009), dissertation, University of Michigan).

Preconcentration can be achieved using chemisorptions or physisorption. Because chemical adsorption requires covalent bonding and breaking of covalent bonds, physical adsorption is typically preferred. Physisorption can involve both absorption and adsorption, in for example, liquids or cold surfaces. However, liquid sorption or cold sorption are difficult to employ in microdevices. A number of different compounds have been used as adsorbents in microdevices, including activated or graphitized carbon, polymeric compositions (e.g., Tenax TA, see, e.g., Alfeeli B., et al. Solid State Sensors, Actuators and Microsystems Workshop Hilton Head Island, South Carolina, Jun. 1-5, 2008, pages 118-121), and surfactant-templated sol gels (see, e.g., Manginell, R. P. et al. Tech. Digest 2000 Sol.-State Sensor and Actuator Workshop Transducers Research Foundation, (2000):179-182 and U.S. Pat. No. 7,118,712, incorporated herein by reference in its entirety for its technical disclosure). Non-limiting examples of adsorbents include: porous polymers such as Tenax TA, Tenax GR, Dow XUS493, and Dow XUS565; graphitized carbon such as Carbopack B, Carbopack X, Carbopack Y, and Carbotrap C; carbon molecular sieves such as Carboxen 569, Carbosieve SIII, and Carboxen 1000; and thick-film polymers such as styrene divinylbenzene and vinylpyridine-divinylbenzene.

Analyte typically is desorbed from an adsorbent material by heating (thermal desorption) although other methods are not excluded. In a typical design of a useful heating element (often referred to as a 'hotplate"), the adsorbent is manufactured onto a resistive or infrared heating element. Manginell, R. P. et al. disclose a thin-film platinum heater deposited onto silicon nitride. Creemer et al. (Proceedings Semiconductor Advances for Future Electronics (SAFE), Veldhoven, the Netherlands, 2004, pp. 742-746) disclose a TiN heating element deposited onto (low-stress) silicon nitride, and also describes a $Ta_5Si_3$ heating element. Spannhake et al. (*Sensors* 2006 6:405-419) disclose silicon-on-insulator infrared heating elements (Pt, PtSi, Si:B and $SnO_2$:Sb) and designs therefor. See, generally Rodríguez et al. (cited above) for a general summary of preconcentrator heating element configurations.

As disclosed in U.S. Pat. No. 6,171,378, incorporated herein by reference in its entirety for its technical disclosure, chemically-selective sorptive coatings are well-known in the art and have been previously used, for example, to selectively sorb particular chemical species on acoustic wave sensors for detection by mass loading. See, for example, an article by M. S. Nieuwenhuizen et al entitled "Surface Acoustic Wave Chemical Sensors," in Sensors and Materials, vol. 5, pp. 261-300, 1989 which discloses different types of polymers which can be prepared to selectively sorb particular chemical species, including polymers which selective sorb a nerve agent simulant dimethyl methyl phosphonate (DMMP). The preparation of surfactant-templated microporous oxides (including silicon dioxide which is also termed silica) based on sol-gel oxides have been disclosed in an article by N. K. Raman et al entitled "Template-Based Approaches to the Preparation of Amorphous, Nanoporous Silicas," in Chemistry of Materials, vol. 8, pp. 1682-1701, 1996; and in another article by Y. Lu et al entitled "Microporous Silica Prepared by Organic Templating: Relationship Between the Molecular Template and Pore Size," in Chemistry of Materials, vol. 11, pp. 1223-1229, April 1999. The preparation of other microporous sol-gel oxides are disclosed in an article by G. C. Frye et al entitled "Controlled Microstructure Oxide Coatings for Chemical Sensors," in Proceedings of the 1990 Solid State Sensors and Actuators Workshop, pp. 61-64, IEEE, New York, 1990; in U.S. Pat. Nos. 5,224,972 and 5,589,396 to Frye et al; and in U.S. Pat. No. 5,770,275 to Raman et al.

U.S. Pat. No. 7,118,712 describes a method useful in preparing a preconcentrator structure based on a (polycrystalline) silicon chip. A thermal oxide etch stop layer (e.g., 0.5 μm thickness) can be grown and a silicon nitride membrane layer can be deposited by LPCVD on the front side of a silicon wafer. A resistive heating element can be formed on the silicon nitride membrane layer by a lift-off process. A layer of photoresist can be spin-coated and patterned to expose the silicon nitride layer. A metallic resistive heater layer is then deposited on the developed photoresist layer. The resistive heater layer can be a 0.35-μm-thick layer of platinum sputter-deposited on a 10-nm-thick chromium adhesion layer. Metal deposited over the remaining portions of the photoresist can be removed by lift-off of the photoresist, using acetone solvent. Similarly, a metallic bond pad layer (e.g., a 1-μm-thick layer of gold e-beam evaporated on a 10-nm-thick chromium adhesion layer) can be deposited and patterned on the silicon nitride membrane layer by a lift-off process to form the bond pads. A hardmask layer (e.g., a 0.1-μm-thick layer of e-beam evaporated titanium) can be deposited and patterned on the frontside of the silicon wafer by a lift-off process. The titanium hardmask can be patterned to define various structures of the silicon nitride membrane layer that are to be later removed. A photoresist can be spun on the frontside to protect the hardmask and the resistive heating element during subsequent high-aspect-ratio etching (e.g., a "Bosch" deep reactive ion etch) of the backside. A photoresist can be spun on the backside and patterned to provide a mask for the subsequent Bosch etch. The Bosch mask defines a sorption support structure and may be aligned to the pattern of the resistive heating element on the frontside of the silicon wafer. The exposed backside silicon can then be removed by Bosch etching, stopping on the oxide layer, to provide the sorption support structure. The frontside photoresist and the remaining backside photoresist can then be stripped. The exposed silicon nitride can be removed by dry etching in a $CF_4/O_2$ plasma through the frontside titanium hardmask to provide annular openings in the membrane. Exposed oxide and the titanium hardmask can be removed with a buffered oxide etch comprising HF.

Figure 8:
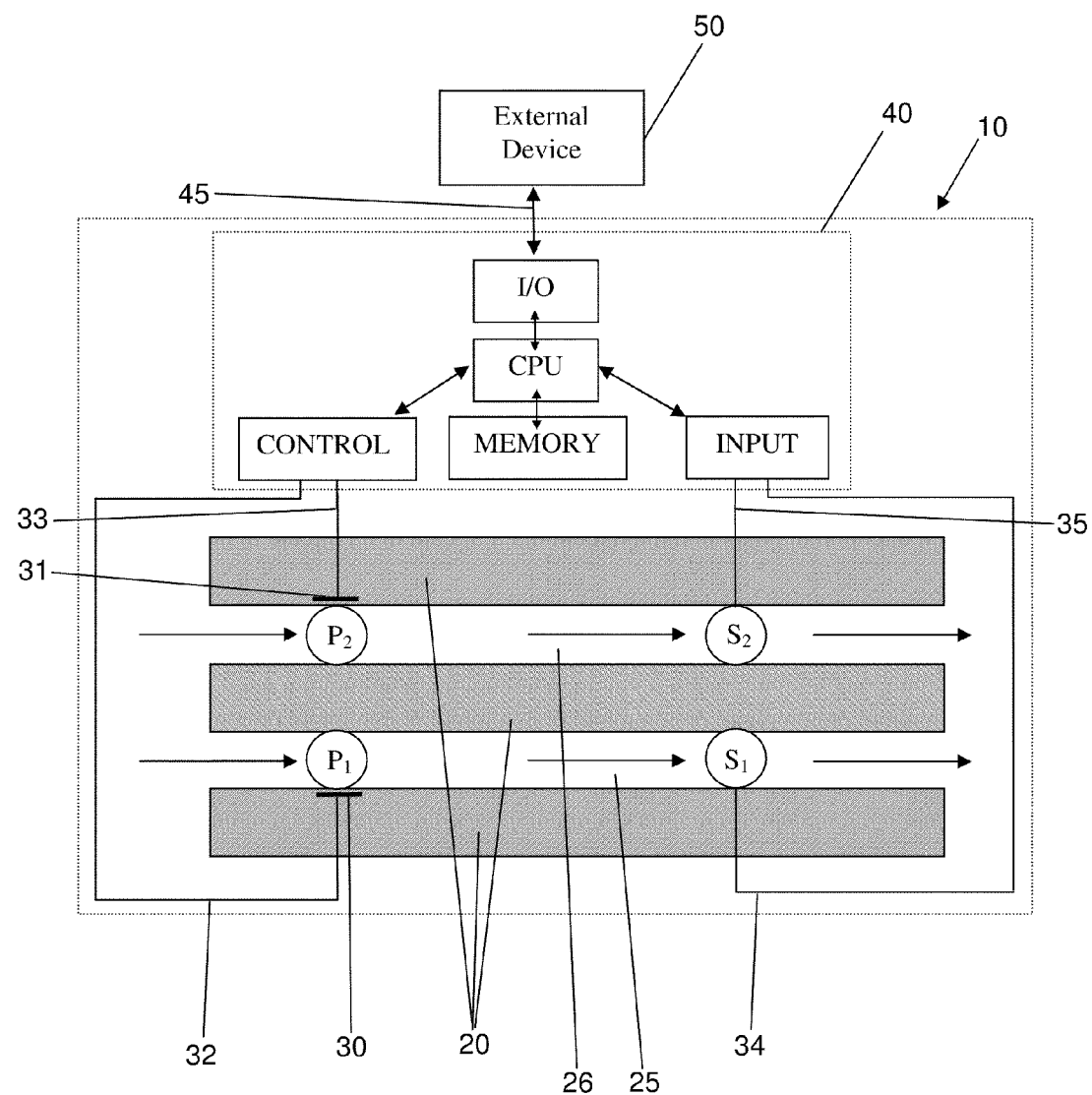
FIG. 8 is a schematic diagram of one embodiment of a sensor device and sensor system as described herein.

The devices described herein can be prepared according to standard MEMS, IC, PCB, etc. design and manufacturing methods and criteria. Electronic circuits can be integrated into the device according to known methods. The devices can be packaged in any suitable manner providing for efficacy of the sensors and overall function of the devices. FIG. 8 is a schematic of a typical device 10. As should be recognized by those of ordinary skill in the art, considerable variation in the layout and components of such a device would result in equivalent functionality. As shown, the device 10 comprises a substrate 20 comprising two channels 25 and 26. Preconcentrators are designated $P_1$ and $P_2$. Sensors are designated $S_1$ and $S_2$. $P_1$ and $S_1$ are located in proximity to channel 25 and $P_2$ and $S_2$ are located in proximity to channel 26. Sensors and preconcentrators, while being shown within channels 25 and 26 may be placed within a wall of channel or otherwise in proximity to channels 25 and 26 to permit functionality. Preconcentrators are shown upstream to sensors, with "upstream" referring to the direction of flow of gas through the channel, such that gas flows in an upstream-to-downstream direction. Preconcentrators $P_1$ and $P_2$ typically comprise a sorbent material to adsorb one or more analytes. Heating elements 30 and 31 are provided in proximity to preconcentrators $P_1$ and $P_2$ to heat preconcentrators $P_1$ and $P_2$ to desorb analyte from the sorbent substrate.

Leads 32 and 33 are electrically connected to heating elements 30 and 31 to power the heating elements. Leads 34 and 35 are connected to sensors $S_1$ and $S_2$ to transmit data from the sensors $S_1$ and $S_2$ and to an "INPUT" of sensor computing device 40. The "INPUT" of sensor computing device 40 may comprise one or both of an amplifier (e.g., operational amplifier, preamplifier, differential amplifier, etc.) to amplify signal from the sensors and an analog-to-digital chip/circuit to convert raw analog data obtained from sensors to a digital format.

The "CONTROL" of sensor computing device 40 comprises computer software ("software" (or computer software) includes, without limitation: application software, middleware, computer processes, programming languages, code, system software, operating systems, testware, firmware, device drivers, programming tools, data, etc. for carrying out a specific task) and/or computer hardware for controlling the timing and optionally the intensity of the heating of heating elements 30 and 31 and therefore preconcentrators $P_1$ and $P_2$ to desorb analyte adsorbed into preconcentrators $P_1$ and $P_2$. Useful computer software and/or hardware constituents are readily developed by those of ordinary skill in the related arts, such as using assembly language on a microcontroller, or using any of a large variety of available programming resources, languages, for example and without limitation: C, Matlab and Java.

As described herein, according to one embodiment, the heating elements 30 and 31 alternately heat one or more times for a suitable duration to desorb analyte. Sensors monitor gas flowing through channels 25 and 26 either continuously or periodically, for example for a designated amount of time following heating of either preconcentrator. Sensors can monitor one or both channels simultaneously or according to any effective timing scheme.

In an alternative embodiment (not shown), in reference to FIG. 8, one or more heating elements are placed in proximity to (adjacent to) the sensors S1 and S2. The heating element(s) adjacent to the sensors can be activated individually or concurrently at any suitable time in relation to the use of the sensors to detect/measure analyte and/or desorption of analyte from the preconcentrator(s); for example, immediately prior to heating of the preconcentrator(s) by heating elements 30 and 31.

Also in reference to FIG. 8, but not shown, sensors to monitor flow rate can also be placed in proximity of channels 25 and 26 and signals can be routed to the sensor computing device 40. These flow sensors can be used to trigger the turn-on of the heaters 30 and 31 of the preconcentrators at a given flow rate. For example, in a gas respirator application a variable flow through the channels can be created by human respiratory action (i.e., breathing). The flow sensors can detect a certain flow rate appropriate for the preconcentrator function. This flow rate, for example, can be below 10 milliliters/min for micro-scale preconcentrators, which is relatively low compared to an average human breathing flow rate of 32 liters/min.

The sensor computing device 40 comprises a central processing unit ("CPU") and "MEMORY" which stores data collected and any useful computer software (e.g. firmware) for controlling device 10 and for obtaining, converting, analyzing, storing and uploading data. Memory may comprise of any useful data storage device, including ROM, PROM, FPROM, OTP NVM, RAM, EEPROM, flash memory, etc. Because the device in many instances is miniaturized, the memory component is, to the extent possible, miniaturized. The CPU can comprise of any useful processing circuitry, chip (microprocessor)/hardware/software, combinations etc. The sensor computing device 40 also typically comprises an input/output interface ("I/O" or communications interface), such as a wired interface such as a USB, serial, parallel or firewire interface, or a wireless interface, such as a Bluetooth interface or a RFID-based interface for communicating with an external device 50, which can be a second computing device (e.g., PC, laptop, smartphone, PDA, tablet PC, iPad, etc.) for uploading data, analyzing data, outputting data, downloading firmware to the device 10, or for any activity. Device 10 can be powered by batteries (not shown), such as rechargeable batteries (e.g., via a USB interface) or any suitable power source.

The device as shown in FIG. 8 is suitable for use in a remote sensor, such as for monitoring analyte levels in a gas mask or filtration device to determine the presence of environmental contamination, the status of adsorbant levels in the mask (indicating breakthrough of, e.g., VOCs), or to monitor a subject's respiration. As such, the miniaturized device 10 can be installed in a gas mask, and analyte levels can be monitored in the manner indicated and the results stored within the system memory. Periodically or continually the data can be uploaded to an external computing device for monitoring, analysis, storage, etc.

Signal received from sensors $S_1$ and $S_2$ is optionally converted to a digital signal, but conversion to a digital signal may be preferred in certain embodiments. In order to obtain quality information from the device, the signals from sensors $S_1$ and $S_2$ are compared by differencing the output of the sensors either by analog or digital processing. Where data is obtained remotely and transferred to a second computer as is illustrated in FIG. 8, the differencing can be performed either at the sensor computing device or external device. It may in many instances be in such a configuration to conduct the differencing at the sensor computing device, though if a real-time connection (typically wireless, including substantially real-time connection, meaning that data is transferred from the sensor device to the external device regularly, such as every second, 10 seconds, minute or even hourly or daily depending on system tolerances) between the sensor and external device is used, differencing and comparison against reference data, if used, can be conducted in one or both of the sensor and external devices in a stand-alone or distributed manner. Alarm functions, indicative of analyte levels reaching a desired threshold, may be programmed or otherwise incorporated into the devices described herein to provide a discernable signal indicating crossing of a threshold. One non-limiting example of such a threshold is an increase in analyte concentrations in a gas sample indicative of VOC breakthrough in a gas mask indicative of loss of function of an adsorbant material in the gas mask.

Figure 9A:
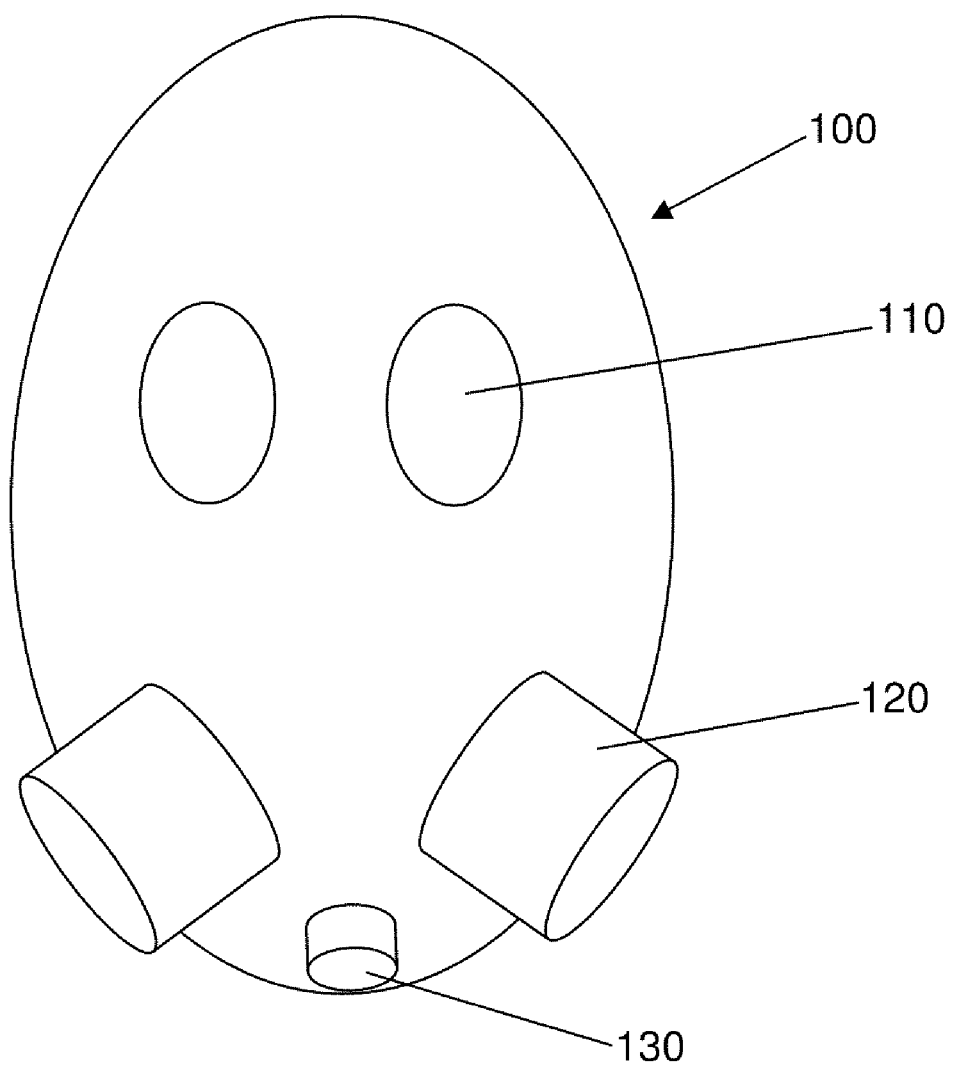
FIG. 9 is a schematic diagram of a gas mask comprising one embodiment of a sensor as described herein.
Figure 9B:
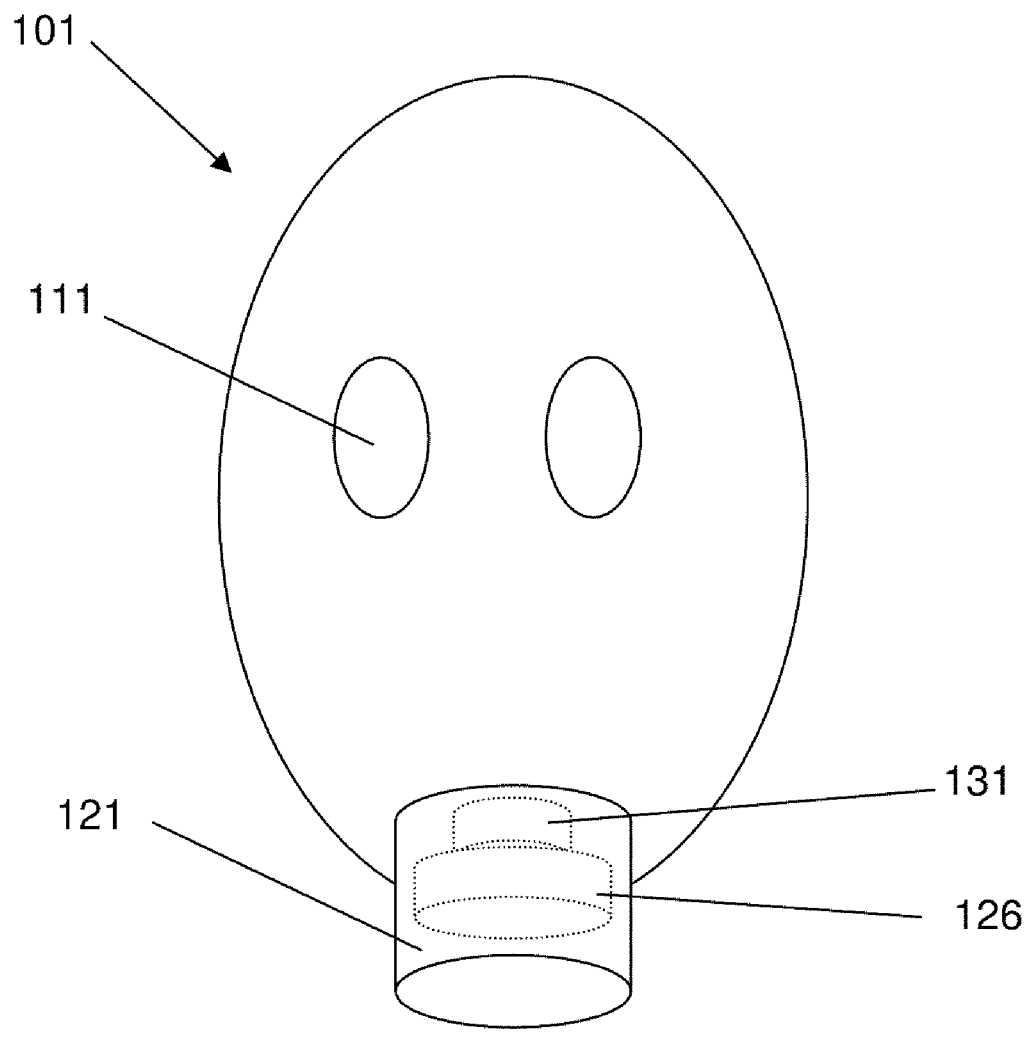

FIGS. 9A, 9B, 10A and 10B are simplified schematic diagrams of gas mask/respirator structures comprising a sensor device as described herein. FIG. 9A illustrates a gas mask 100 showing transparent eye windows 110, filtration canisters or cartridges 120 and sensor device 130. Pressure differentials from inhaling and exhaling can cause air/gas to pass through the sensor device 130. As described above, the sensor device may comprise on-board computer and communications functions. Given the ability to micro-manufacture the device, e.g., with MEMS and/or NEMS processes, the device may be quite small in relation to the size of the mask. Alternately, as shown in FIG. 9B, the sensor device may be placed inside the mask, for instance within the canister structures 120 so that air passing through the canisters also pass through the mask 101, comprising eye windows 110 and a single canister 121, comprises within the canister 121 a filtration media canister 126 and sensor device 131. This in-line configuration is particularly useful for sensing analyte (e.g., VOC) breakthrough indicative of failure or imminent failure of the filtration media.

Figure 10A:
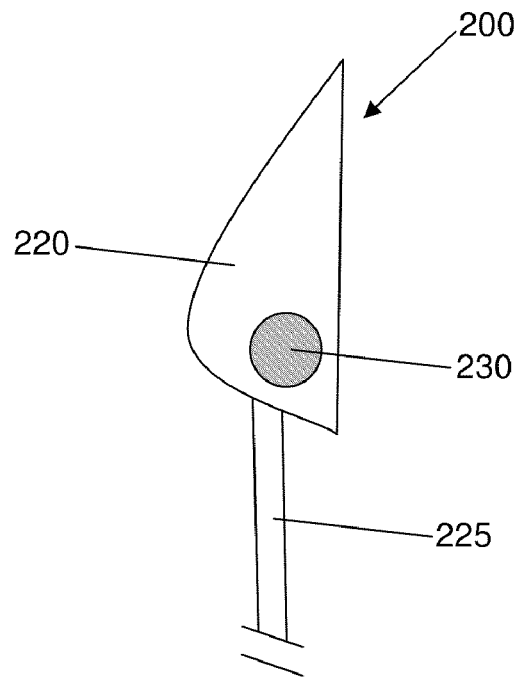
FIGS. 10A and 10B are alternate embodiments of a respirator mask comprising an embodiment of a sensor as described herein.
Figure 10B:
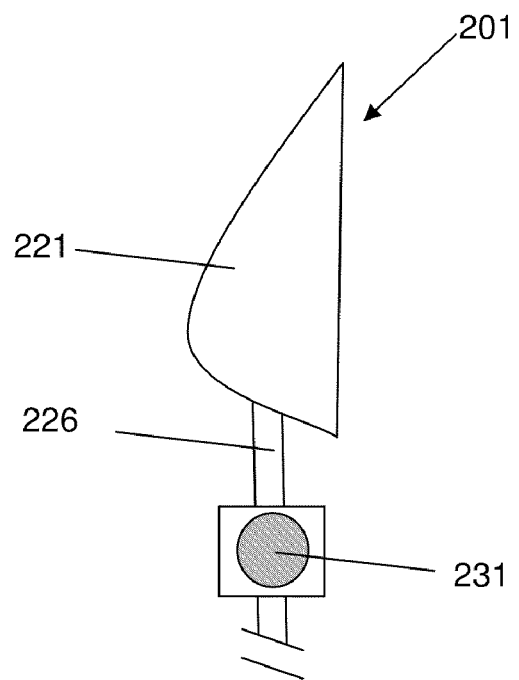

FIGS. 10A and 10B show alternate embodiments of a breathing mask 200 and 201, respectively, comprising a mask portion 220 and 221, respectively, and a gas feeder tube 226 and 226, respectively. In FIG. 10A, sensor device 230 is integral with the mask portion 220, while in FIG. 10B, sensor device 231 is shown in-line with the gas feeder tube 226.

As described herein, over a single measurement cycle, the preconcentrator in one channel $P_1$ releases its concentrated analyte for the chemical sensor in that channel to detect $S_1$. During cycle #1, the sensor $S_2$ in the second channel is used as a reference. The next measurement cycle (#2), the preconcentrator in the second channel $P_1$ releases its concentrated analyte, and the roles of the two chemical sensors are reversed. Because both chemical sensors are equally exposed to analyte on average, they should age similarly. This means that the reference in each measurement remains accurate over time, since the reference remains a similarly behaving chemical sensor. The effect of ageing will be reduced, and the long term stability of the sensor will be significantly improved.

Figure 1:
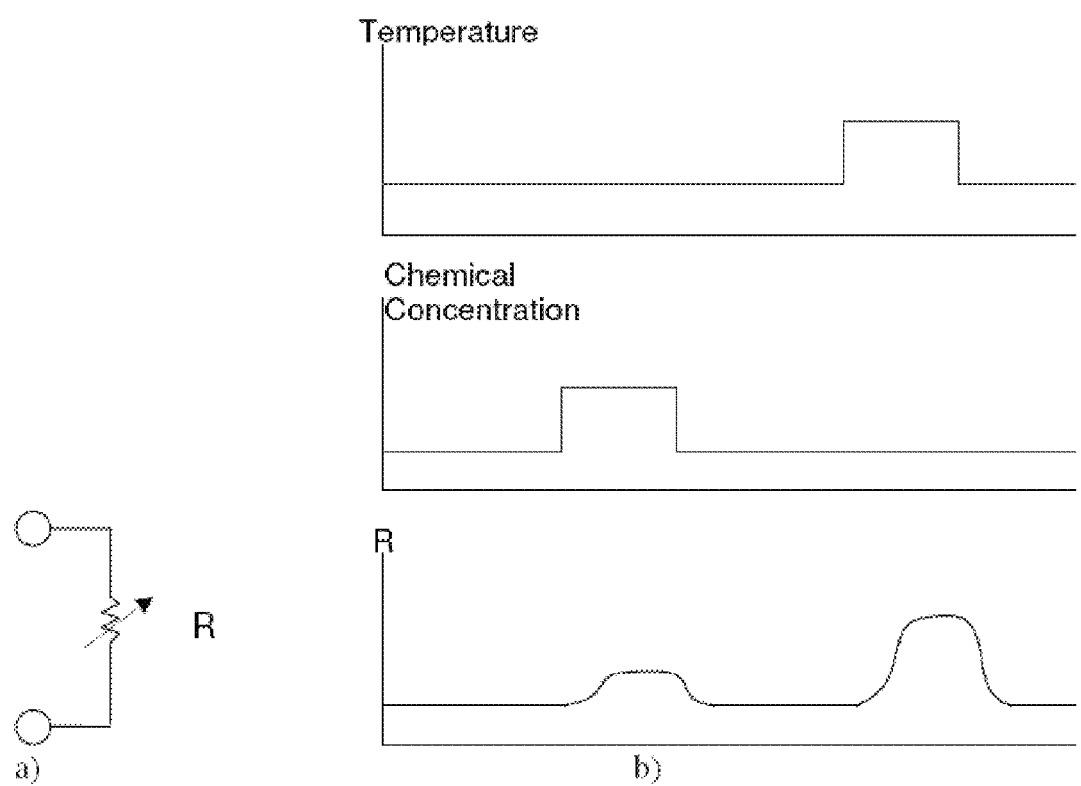
FIG. 1 illustrates the limitations of prior art sensors in distinguishing between changes in temperature and changes in the chemical analyte concentration.
Figure 2:
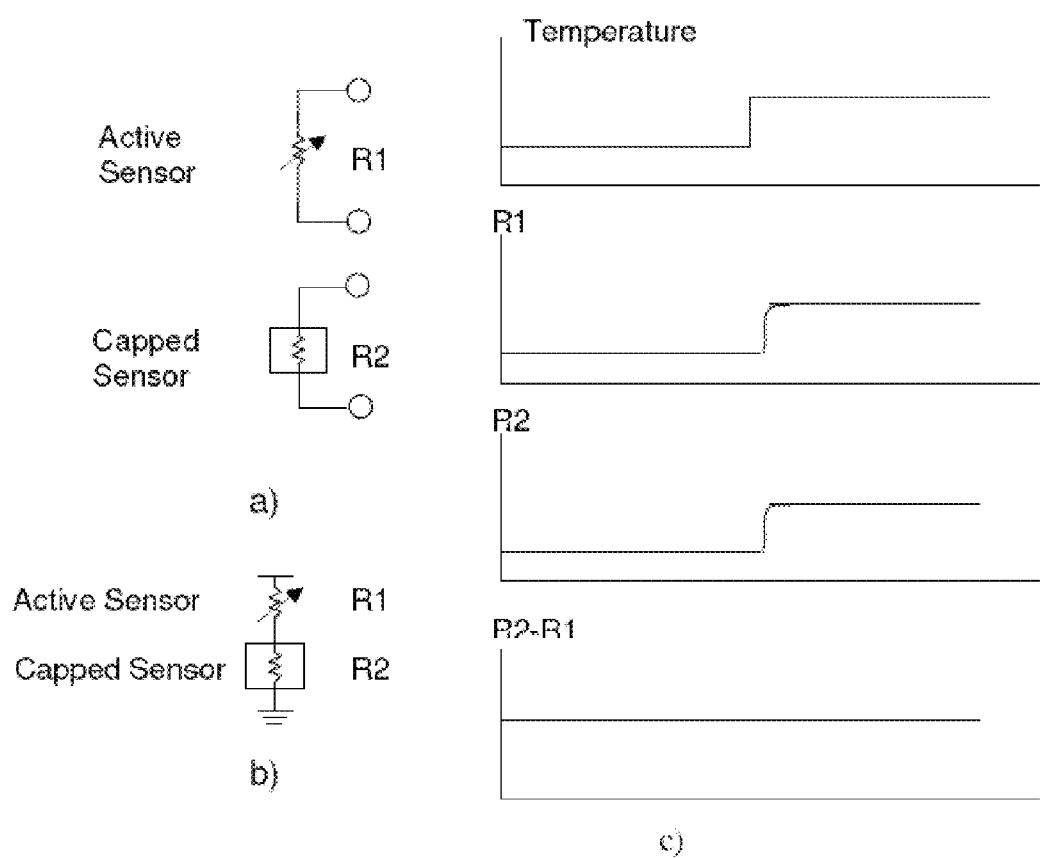
FIG. 2 illustrates the use of reference sensors in an ideal situation where there is no difference in responses from the active and reference sensors.
Figure 3:
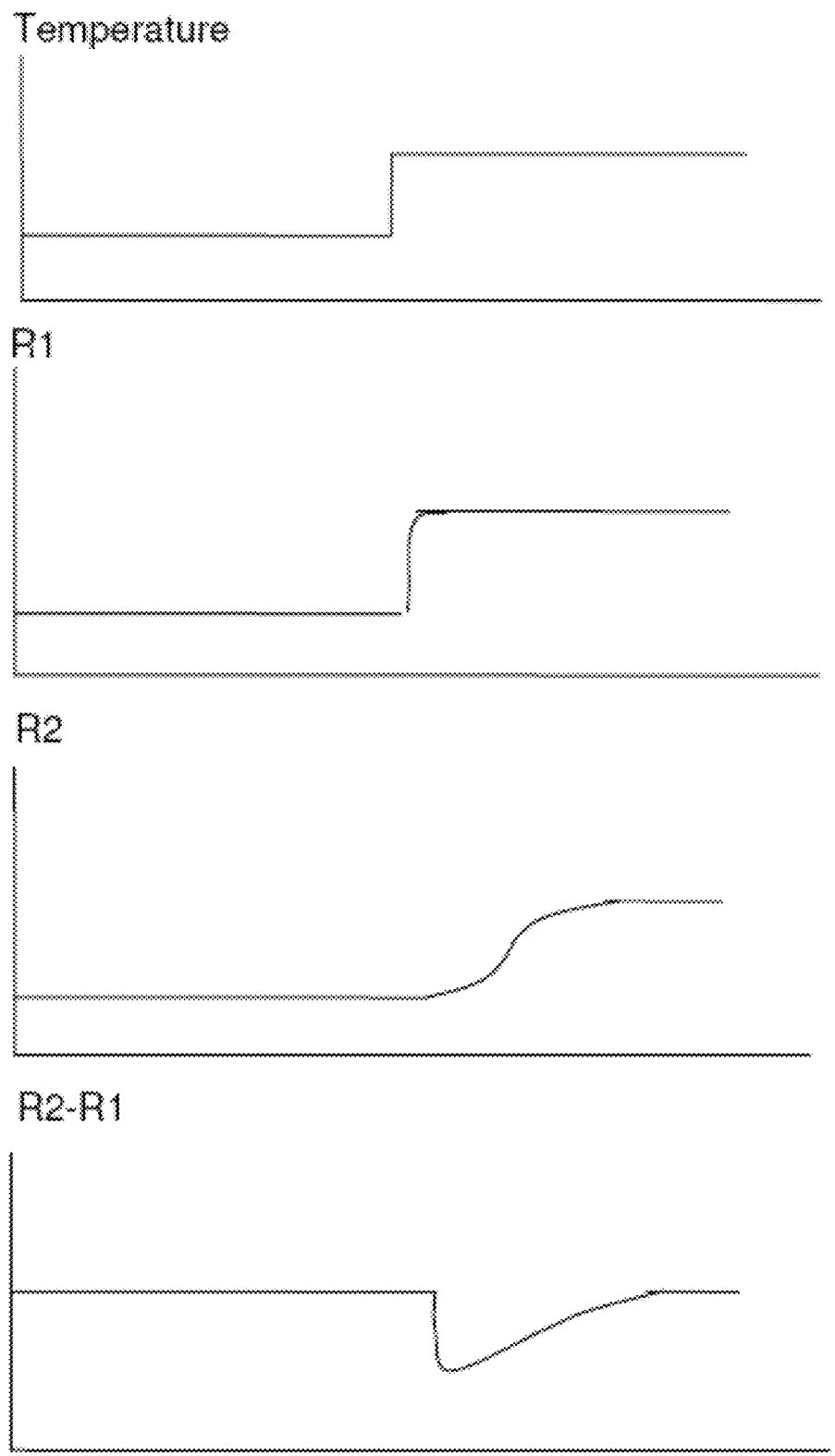
FIG. 3 illustrates the limitations of prior art sensors which have a capped reference sensor.
Figure 4:
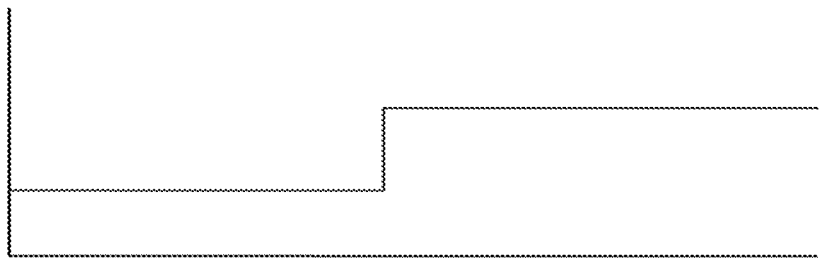
FIG. 4 illustrates the limitations of prior art sensors which have a capped reference sensor which is infiltrated by humidity.
Figure 4:
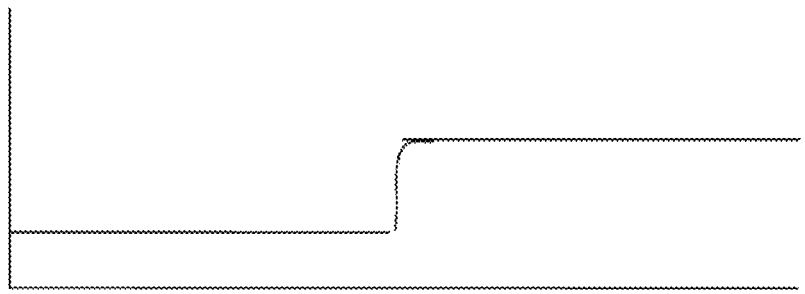
Figure 4:
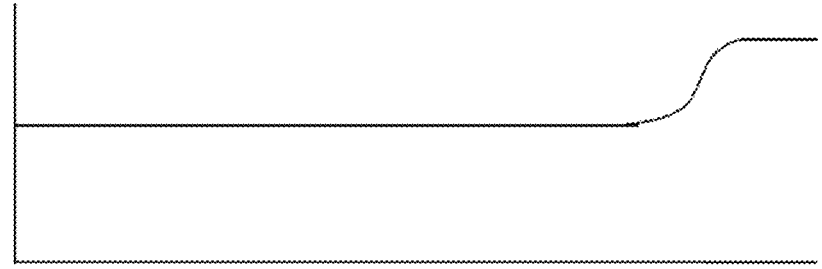
Figure 4:
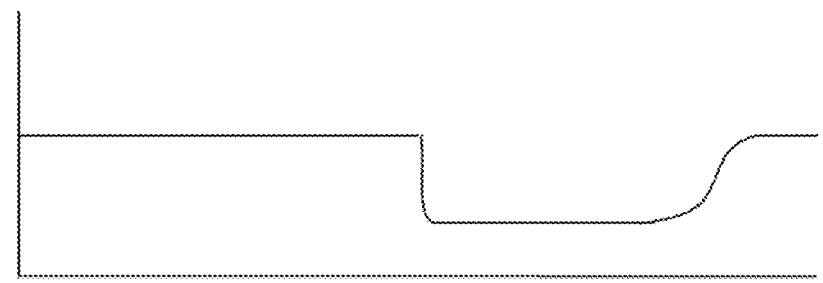
Figure 5A:
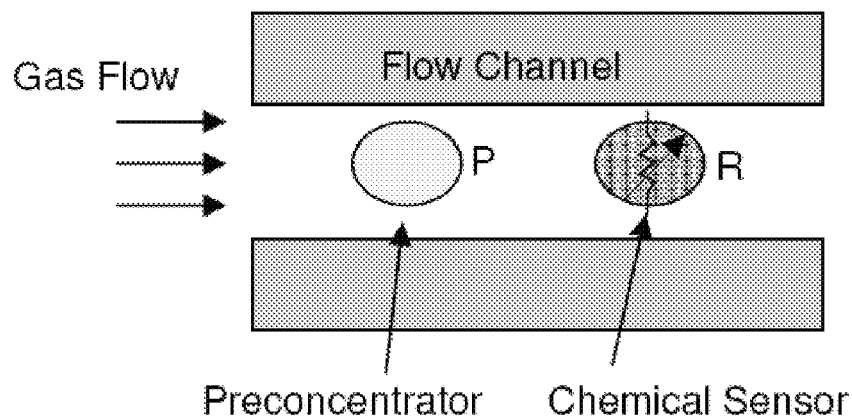
FIGS. 5A and 5B illustrates the prior art concept of using preconcentrators in sensors.
Figure 5B:
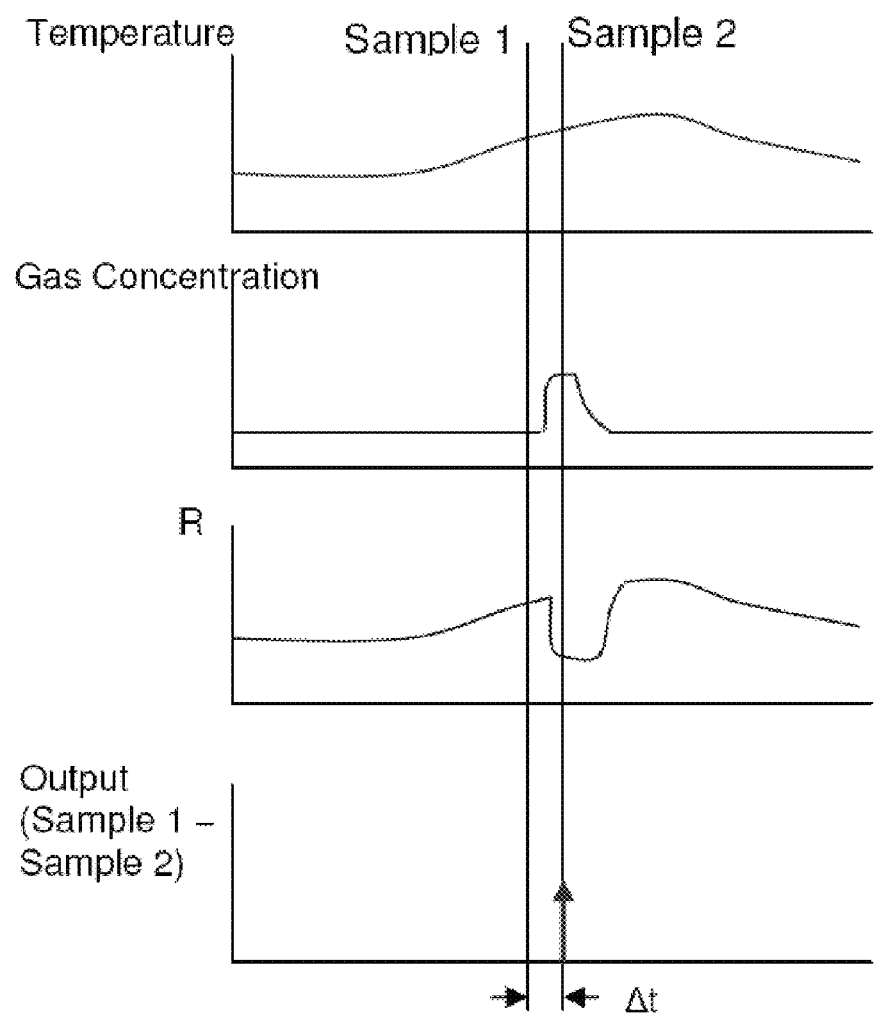
Figure 11:
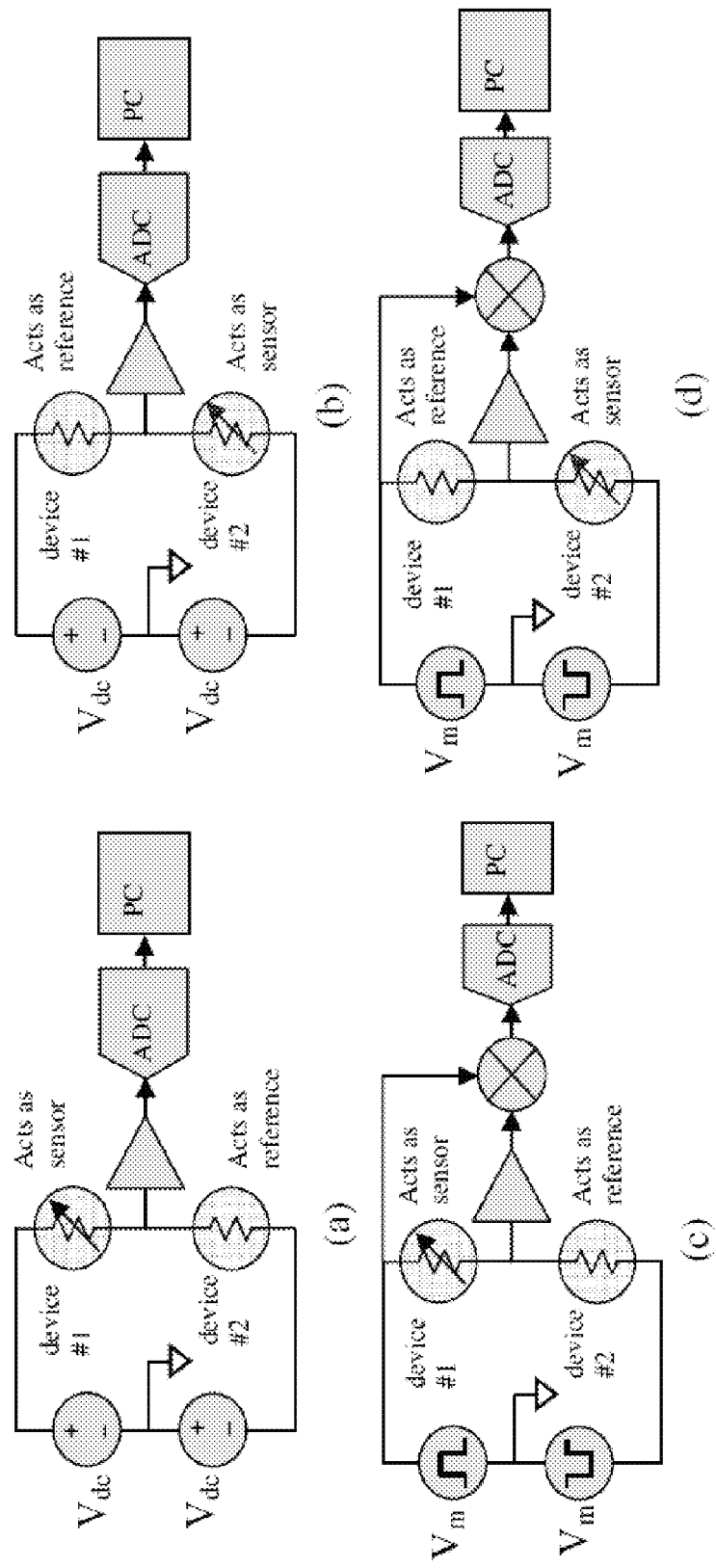
FIG. 11 provides sensor circuit diagrams for single-sided chemiresistive dividers. (a) DC voltage input, preconcentrator cycle #1, (b) cycle #2, (c) AC modulation input, preconcentrator cycle #1, (d) cycle #2.

The differential sensor scheme can be used for any chemical sensor device, including chemiresistive sensors (See Example 1), chemical field-effect transistors, chemicapacitive sensors, gravimetric sensors, heat of adsorption sensors, optical sensors and surface plasmon sensors. Those skilled in the art will recognize that many other chemical sensors would benefit from this approach. A specific embodiment of a differential sensing system using chemiresistors in shown in FIG. 11. Device #1 is located in one channel with a preconcentrator, and device #2 is in a second channel with its preconcentrator. FIG. 11 (*a*) shows a resistive divider circuit driven by a dc voltage. This circuit can easily be extended to a full bridge if desired. Device #1 is activated as a sensor by turning on its preconcentrator in cycle 1 of the timing diagram in FIG. 7. FIG. 11 (*b*) shows the schematic during cycle #2 of FIG. 2. FIGS. 11 (*c*) and (*d*) show schematics of the sensing circuit driven by a modulation voltage instead of a dc voltage. The modulation voltage may be beneficial in eliminating low frequency noise (e.g. flicker noise) in the output voltage. Those skilled in the art will recognize that many other circuit embodiments can be used to measure the output voltage or current from the resistive divider. Alternative embodiments can measure the resistance of $R_1$ and $R_2$ separately as in FIG. 2 and then difference with analog or digital logic.

The current invention is novel in providing differential chemical measurement between a sensor and a reference where both devices experience the same environment when averaged over time. This is accomplished through swapping the roles of sensor and reference periodically. The advantage is in the superior matching over time of the sensor and reference. This is potentially advantageous over prior art low cost chemical sensor systems.

The embodiment with separate gas channels and preconcentrators to implement the periodic swap of the sensor and reference is also novel. In contrast to prior methods, the new differential scheme enables differencing of signals at the same period in time in any given measurement cycle. The differencing can then be accomplished in situ in the analog circuit, eliminating the need to difference large values to arrive at the compensated output. Any form of analog differencing circuit can be used. Possible examples include the resistive divider from FIG. 2, for resistive chemical sensors, a capacitive divider for capacitive sensors, and various circuits for subtracting frequency for sensors that depend on the measurement of a resonant frequency, such as a gravimetric sensor. The outputs could also be converted to digital signals, and subtracted using digital logic.

Example 1

Jetted Nanoparticle Chemical Sensor Circuits for Respirator End-of-Service-Life Detection Gold nanoparticle chemiresistors, formed by ink-jetting onto spiral gold electrodes, were explored for use as respirator cartridge end-of-service-life indicators. Two 250 µm-diameter chemiresistors are connected electrically in a half-bridge circuit, with one capped as a reference. Output sensitivity is −123 µV/ppm for toluene. Breakthrough of 500 ppm toluene in a carbon cartridge simulator was demonstrated.

As proof of concept with respect to the ability to fabricate a sensor comprising the described components, gold nanoparticles protected with 1-octanethiol (C8) were synthesized by the single-phase method of Rowe et al. (Chem. Mater., 16 (2004), 3513-3517). Two nanometer-diameter nanoparticles were mixed in 1,2,4-trichlorobenzene (TCB) at a 5 to 10 mg/ml concentration. The solution was loaded into a custom inkjet system with a 30 µm-diameter piezoelectric drop-on-demand jet nozzle (MicroFab Technologies, Plano, Tex.) that ejects drops on the order of 30 picoliters. The inkjet system includes computer vision calibration to position drops within 2 µm of targets (L. Weiss, L.Schultz, and E. Miller, "Inkjet deposition system with computer vision-based calibration for targeting accuracy," Robotics Institute Tech. Report, CMU-RI-TR-06-15V2A (2007)). The silicon device substrate is covered by a 1 µm-thick silicon dioxide layer. Spiral interdigitated 75 nm-thick gold electrodes on a thin Ti adhesion layer are patterned by a combination of ion milling and wet etching. The completed electrodes are 3 µm wide with 4 µm spacing, and span a diameter of 250 µm, as shown in FIG. 12(*a*).

The inner 200 µm diameter of electrodes form the chemiresistor. The remaining 50 µm annular area surrounding the active electrodes houses electrically neutral "guard ring" electrodes. The guard rings ensure that splats cover the active electrodes and result in on-chip resistance matching to better than 10%.

Figure 12:
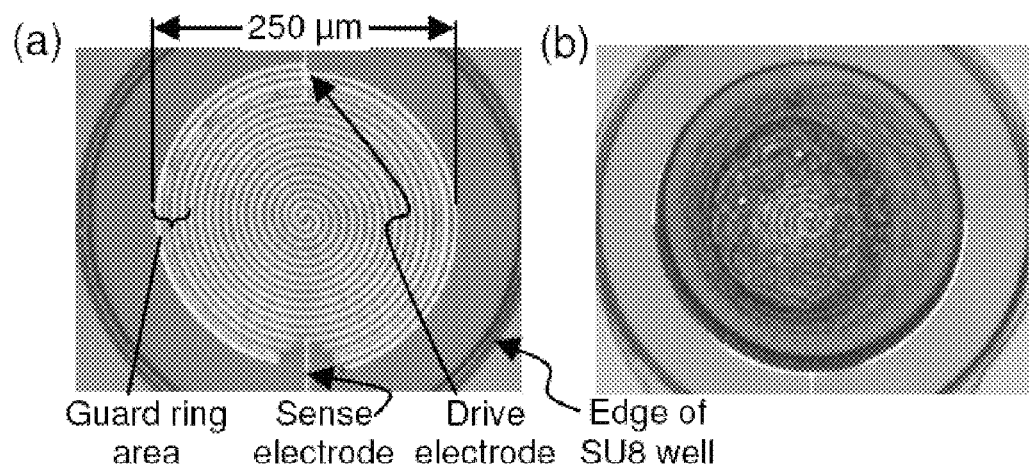
FIG. 12 are photographs of spiral interdigitated electrode chemiresistors: Chemiresistive splat made from (a) 15 drops of solvent with nanoparticle solute and (b) 225 drops of solvent with nanoparticle solute, as described in Example 1.

Two example splats after drying are shown in FIG. 12. The splat in (b) has an estimated film thickness of 1.5 µm. The deposited solvent puddle initially extends beyond the electrodes and later pulls back within the electrode boundary. The axi-symmetric and regular electrode layout ensures uniform surface tension effects.

Figure 13:
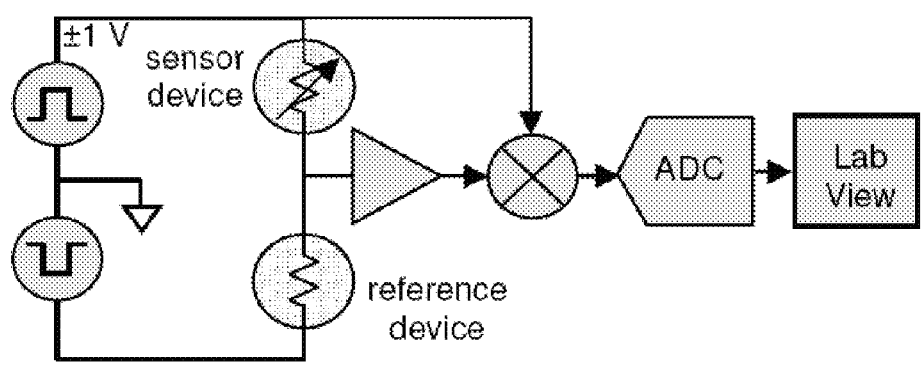
FIG. 13 provides a sensor circuit diagram as described in Example 1.

The TCB puddle takes several seconds to evaporate, allowing the nanoparticles precipitate into a thin film with minimal "coffee ring" effects. The jetted splats are dried in a vacuum oven at 40° for 4 hours. The sensor output is generated from a circuit shown in FIG. 13.

Figure 14:
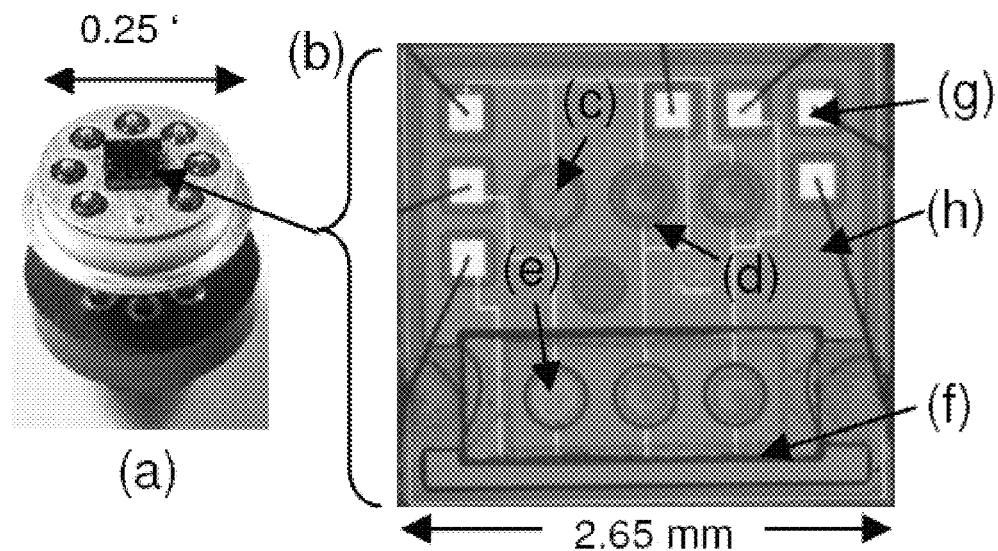
FIG. 14 are photographs of a silicon sensor chip with three chemiresistive half-bridge circuits, as described in Example 1: (a) TO-5 package. (b) Chip. (c) Sensor device. (d) Edge of photo-defined epoxy (SU-8) well. (e) Reference device under glass cap. (f) Arathane around glass cap. (g) Bondpad and bondwire. (h) Resistive Temperature Device (RTD) location.

The voltage divider is driven by balanced square-wave modulation that changes from +1 V to −1V every 5 s. The voltage signal is detected using a high-impedance input preamplifier, demodulated and converted to digital format (ADC) through LabView (National Instruments, Austin Tex.) control on a PC. A typical silicon chip structure (for a similar capped resistor device is shown in FIG. 14. The depicted chip comprises three chemiresistive voltage dividers with capped reference devices. The seven bond pads on the chip route the two drive voltages, the three sensor outputs, Vs1, Vs2, and Vs3, and two leads to a gold resistive temperature device (RTD). The chip is patterned with 40 µm-thick SU-8 epoxy to form wells around the devices and to act as interconnect passivation.

Figure 15:
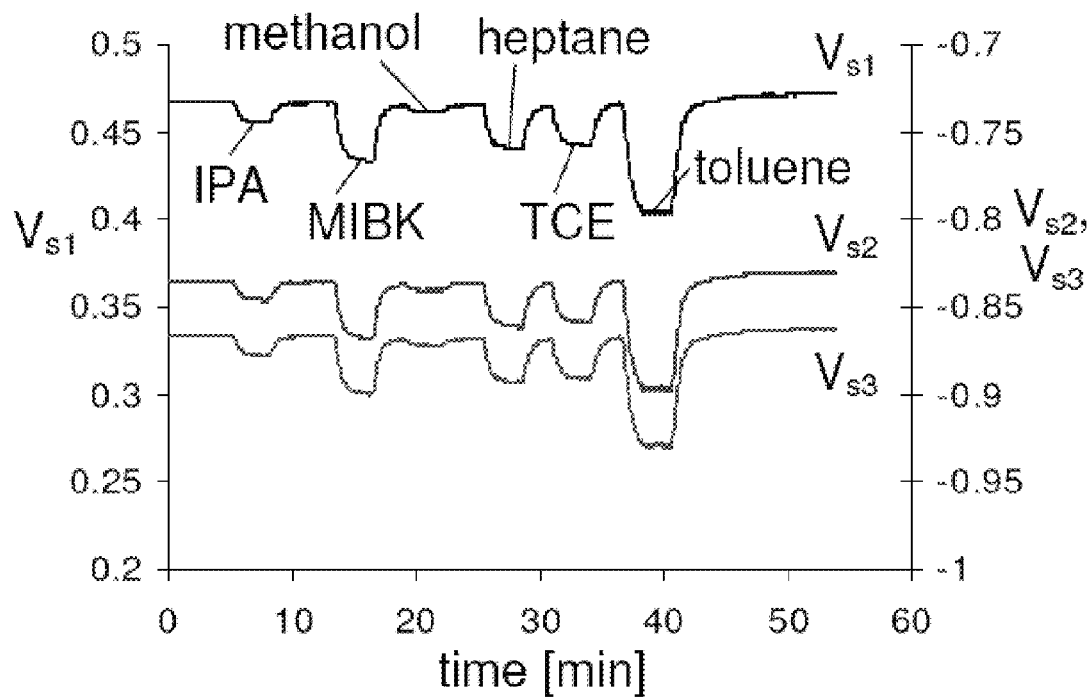
FIG. 15 is a graph showing pulse response of jetted gold nanoparticle sensors to six Volatile Organic Compounds (VOCs) as described in Example 1. Pulses are 500 ppm except methanol at 2000 ppm and methyl isobutyl ketone (MIBK) at 200 ppm.
Figure 16:
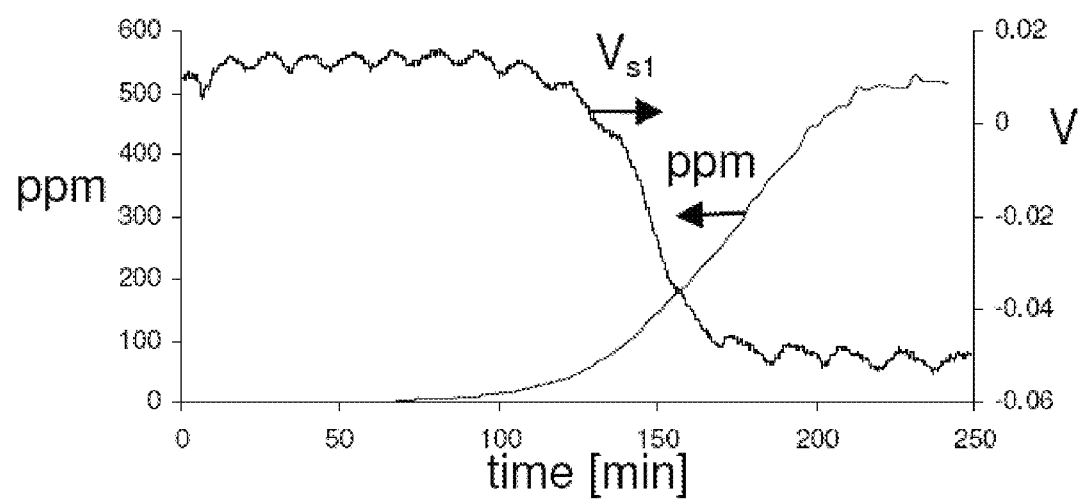
FIG. 16 is a graph showing a cartridge breakthrough curve as described in Example 1.

FIG. 15 shows a typical pulse response for the capped electrode chip shown in FIG. 14, exposed to various organic solvents with a VICI M6 micro-dispensing pump in 32 L/min air flow. The devices have a high sensitivity of −123 µV/ppm toluene and low sensitivity of −2 µV/ppm methanol. Sensitivity matches to within 10% on-chip. FIG. 16 is a breakthrough curve for a sensor embedded in a carbon pack simulating a cartridge. Conditions were 32 L/min air flow, 23% RH and 500 ppm toluene.

Whereas particular embodiments of this invention have been described above for purposes of illustration, it will be evident to those skilled in the art that numerous variations of the details of the present invention may be made without departing from the invention as defined in the appended claims.

We claim:

1. A sensor device comprising a first flow channel and a second flow channel, the first flow channel comprising a first sensor and the second flow channel comprising a second sensor that is essentially the same as the first sensor; a controller for periodically switching flow of analyte through the first and second flow channels whereby the first and second sensors alternately serve as a sensor and a reference; and an analog or digital processor to conduct differencing of signals from the first sensor and the second sensor.

2. The device of claim 1, in which the first flow channel comprises a first preconcentrator and the second flow channel comprises a second preconcentrator and the controller periodically switches flow of analyte through the first and second flow channel by releasing analyte periodically from the first preconcentrator and the second preconcentrator.

3. The device of claim 2 in which each preconcentrator comprises an adsorbant material and a heating element for desorbing analyte from the adsorbant material.

4. The device of claim 3 in which the preconcentrator comprises one or more of a porous polymer, graphitized carbon, a carbon molecular sieve, and a thick-film polymer.

5. The device of claim 3, in which the heating element is a platinum heating element.

6. The device of claim 2 further comprising one or more flow sensors in or about the flow channels and an output signal of one or more of the flow sensors is used to trigger release of analyte from one or more preconcentrator.

7. The device of claim 2 further comprises one or more flow sensors and one or more heating elements adjacent to one or more of the sensors and an output signal of one or more of the flow sensors triggers heating of a sensor to desorb analyte from the sensor.

8. The device of claim 1 further comprising one or more heating elements adjacent to one or more of the sensors and the controller activates the heating elements to desorb analyte from the one or more sensors.

9. The device of claim 1, wherein the processor conducts the differencing by a resistive divider.

10. The device of claim 1, wherein the processor conducts the differencing by a capacitive divider.

11. The device of claim 1, wherein the processor conducts the differencing with measurements of resonant frequency.

12. The device of claim 1 in which the sensors are chemiresistor sensors.

13. The device of claim 12, in which the chemiresistor sensors are gold nanoparticle chemiresistors.

14. The device of claim 1 in which the sensors are chemicapacitor sensors.

15. The device of claim 1 further comprising one or more heating elements adjacent to the sensors and the controller periodically activates the one or more heating elements adjacent to the sensors to desorb analyte from the sensors.

16. The device of claim 1, in which the controller comprises a computer.

17. The device of claim 16, in which the device comprises a data output interface connected to the computer for transmitting data from the device.

18. The device of claim 17 in which the data output interface is a wireless interface.

19. The device of claim 18 in which the wireless interface is one of an IEEE 802.11 or Bluetooth interface.

20. The device of claim 17 in which the data output interface is a wired interface.

21. The device of claim 20 in which the data output interface is a USB, serial, GPIB or Ethernet interface.

22. A gas mask comprising the device of claim 1.

23. A method for chemical sensing in a sensor device comprising a first flow channel and a second flow channel, the first flow channel comprising a first sensor and the second flow channel comprising a second sensor that is the same as the first sensor, the method comprising: a) controlling flow of an analyte through the first flow channel and the second flow channel in a manner such that the first and second sensors alternately function as a sensor and a reference; and b) differencing signals from the first sensor and the second sensor.

24. The method of claim 23, wherein the first and second channels each comprise a preconcentrator upstream to the sensors and flow of analyte through the channels is controlled by alternately releasing analyte from each preconcentrator.

25. The method of claim 24 in which the preconcentrator comprises an adsorbant material and a heating element for desorbing analyte from the adsorbant material.

26. The method of claim 25 in which the preconcentrator comprises one or more of a porous polymer, graphitized carbon, a carbon molecular sieve, and a thick-film polymer.

27. The method of claim 25, in which the heating element is a platinum heating element.

28. The method of claim 24 in which the device further comprises one or more flow sensors and output of one or more of the flow sensors triggers release of analyte from a preconcentrator.

29. The method of claim 24 in which the device further comprises one or more flow sensors and one or more heating elements adjacent to one or more of the sensors and output of one or more of the flow sensors triggers heating of a sensor to desorb analyte from the sensor.

30. The method of claim 23 in which the device further comprises one or more heating elements adjacent to one or more of the sensors and the controller activates the heating elements to desorb analyte from the one or more sensors.

31. The method of claim 23, wherein the processor conducts the differencing by a resistive divider.

32. The method of claim 23, wherein the processor conducts the differencing by a capacitive divider.

33. The method of claim 23, wherein the processor conducts the differencing with measurements of resonant frequency.

34. The method of claim 23, in which the sensors are chemiresistor sensors.

35. The method of claim 34, in which the chemiresistor sensors are gold nanoparticle chemiresistors.

36. The method of claim 23 in which the sensors are chemicapacitive sensors.

* * * * *